(12) United States Patent
Moltran et al.

(10) Patent No.: US 7,942,037 B2
(45) Date of Patent: May 17, 2011

(54) METHOD FOR DETECTING RESIDUES ON A COMPONENT

(75) Inventors: Jorg Moltran, Hamburg (DE);
Christiane Lindauer, Hamburg (DE);
Jurij Barylo, Hamburg (DE)

(73) Assignee: Airbus Operations GmbH, Hamburg (DE)

( * ) Notice: Subject to any disclaimer, the term of this patent is extended or adjusted under 35 U.S.C. 154(b) by 429 days.

(21) Appl. No.: 12/083,075

(22) PCT Filed: Oct. 6, 2006

(86) PCT No.: PCT/EP2006/067143
§ 371 (c)(1),
(2), (4) Date: Apr. 3, 2008

(87) PCT Pub. No.: WO2007/039644
PCT Pub. Date: Apr. 12, 2007

(65) Prior Publication Data
US 2009/0229353 A1    Sep. 17, 2009

(30) Foreign Application Priority Data
Oct. 6, 2005 (DE) .......... 10 2005 048 151

(51) Int. Cl.
*G01N 15/06* (2006.01)
(52) U.S. Cl. .................................. 73/61.71
(58) Field of Classification Search ........... 73/61.71, 73/53.01, 53.07
See application file for complete search history.

(56) References Cited

U.S. PATENT DOCUMENTS

| 4,858,768 A | 8/1989 | Plester et al. |
| 4,996,160 A | 2/1991 | Hausman Hazlitt et al. |
| 5,679,574 A | 10/1997 | Friedman et al. |
| 6,281,020 B1 * | 8/2001 | Usui .................. 436/175 |

FOREIGN PATENT DOCUMENTS

| DE | 693 01 661 | 3/1994 |
| DE | 42 38 755 | 5/1994 |
| DE | 43 30 301 | 3/1995 |
| GB | 2 336 668 | 10/1999 |

OTHER PUBLICATIONS

English translation of Chinese examination report dated Apr. 14, 2010 for CN 200680037031.8.
International Search Report for PCT/EP2006/067143 dated Dec. 19, 2006.

* cited by examiner

*Primary Examiner* — Hezron Williams
*Assistant Examiner* — Tamiko D Bellamy
(74) *Attorney, Agent, or Firm* — Nixon & Vanderhye P.C.

(57) ABSTRACT

The present invention relates to a method for detecting residues on a component and particularly on the surface of the component. In order to also allow the testing of surfaces which are difficult to access, without the apparatus outlay growing, the method according to the present invention comprises the following steps: producing a base solution and a reference solution from water, producing a washing solution by adding fresh solvent to the base solution, filling the component to be tested with the washing solution, wetting the entire inner surface of the component with the washing solution, draining the washing solution out of the component, producing a test solution by adding the washing solution to the base solution, comparing the test solution to the reference solution, and testing whether a turbidity occurs in the mixing zone between the washing solution and the base solution, as proof for lubricant on the surface of the component.

8 Claims, 1 Drawing Sheet

METHOD FOR DETECTING RESIDUES ON A COMPONENT

This application is the U.S. national phase of International Application No. PCT/EP2006/067143 filed 6 Oct. 2006 which designated the U.S. and claims priority to German Application No. 10 2005 048 151.5 filed 6 Oct. 2005, the entire contents of each of which are hereby incorporated by reference.

BACKGROUND OF THE INVENTION

1. Field of the Invention

The present invention relates to a method for detecting residues on a component and particularly on the surface of the component.

2. Discussion of Prior Art

Most components still have residues from the manufacturing after their production. These may be macroscopic or may comprise microscopic changes of the surface. In particular, the surfaces may be chemically contaminated. Depending on its planned use, the component must be freed of the contaminations and cleaned accordingly. However, the type of the contamination must be known beforehand for this purpose. The methods explained in the following are used in the prior art for testing the purity of component surfaces.

In a visual examination of the component with the bare eye, it is examined whether irregularities are recognizable on metallic, glossy surfaces. Depending on the spottiness of the component after the cleaning, it may be decided whether it must be cleaned once again or not. The surface is often not accessible to a visual examination in the interior of a hollow body, so that a visual examination is not possible.

When wiping off the surface (DIN 65078) using special media (papers, filter papers), it is checked whether particles remain adhering on the wiping medium. Wiping off the surface is only possible when the surface to be tested is accessible, however.

In a rapid test method using adhesive strips ("Tesa film test"), a transparent adhesive strip is stuck onto the component. When the adhesive strip is pulled off, dirt located on the surface (above all dust, metal dust, abrasions, chips) remain adhering to the adhesive strip. Subsequently, the adhesive strip is stuck onto a white background, so that the individual dirt particles are well visible, and are then counted under the microscope (number) or measured using a photometer (grayscale).

In the dissolving method in connection with a suitable chemical detection method, the contaminations on the surface are chemically dissolved. The solution may then be examined using a gas chromatogram, for example (EN ISO 9377-2). Alternatively, the solution may be evaporated in a rotation evaporator, for example, and the residue on evaporation is subsequently examined in a downstream method.

The components may be washed using 2-propanol, and subsequently the particles are counted. A disadvantage in this case is that lubricant solutions are not detected when they pass as real solutions into the 2-propanol. Undissolved lubricant escapes detection using the present invention as does particle counting.

In detection of contamination via wettability, the difference of the surface tension with a clean or contaminated surface is exploited (DIN 65079 (12/87), DIN 53364 (06/75), DIN EN 828 (01/98), QVA-Z10-57-00 (08/96)). Specifically, to detect the contamination on this basis, a Fettrot test, a measurement using test inks, a nigrosin test, a contact angle measurement, or the like may be performed.

It is a requirement in all of the methods cited up to this point that the surface to be tested is well visible or that a surface sample may be taken. The lubricant cleanliness of surfaces in the interior of hollow bodies therefore often may not be tested using these methods without further measures, because they are not accessible.

The quantity of contamination may be concluded by determining the weight difference between the cleaned and the uncleaned component ("weighing method"). However, this method is only advisable for small components, since only then may the weighing be performed precisely enough. In addition, the result of weighing is influenced, inter alia, by the ambient humidity and the degree of dryness of a component. Weighing methods are restrictedly suitable or unsuitable for wet components.

Many mineral oil products contain materials which fluoresce or display colors upon irradiation using UV light (ultraviolet). If the suspicion exists that the residues on the components comprise materials of this type, such a UV test may be used for detecting the contamination. However, the chemical composition of the lubricant limits the applicability of this method. The presence of a suitable measuring apparatus is also a requirement.

Clean sheet steel forms an adherent copper coating in acidic copper sulfate ($CuSO_4$) solution (concentration approximately 25 g/l), since copper is the more noble metal. A discoloration may thus be observed in a copper sulfate test. It is to be clarified in the specific case whether this method may be applied with relatively noble steels. Because of the toxicity of copper ions and the possible influence on the tendency toward corrosion of the materials used in conductive connection to copper, copper sulfate is precluded for use in the drinking water system.

In the "Berlin blue test", the component to be examined is laid in an indicator solution (Berlin blue) or has a droplet of this indicator solution dripped on it. If the surface colors blue, it is not passive. The "Berlin blue test" is based on the formation of chemical compounds which the clean steel surfaces form with iron. A color reaction occurs. However, this may be more difficult or impossible to observe on the inner surfaces of hollow components. The influence of a reaction of the material with iron (II) and iron (III) ions may restrict the applicability of the Berlin blue test, however.

In an electrolyte, electrochemical procedures, which may provide information about the state of the surface (active or passive), occur on a metallic conductive surface upon the presence of a current or voltage. In anodic polarization measurement, an electrolyte droplet is applied between component surface and counter electrode and a current source is connected between component and counter electrode. The time curve of the resulting voltage and the current flowing is recorded and is used as the basis for judging the surface state. Two method variations are differentiated the two electrode technique and the three electrode technique. The apparatus outlay required for performing the measurements is relatively large, however.

In particular residues in the form of nitrite layers are analyzed using glow discharge spectroscopy. However, only relatively thick layers in the μm range may be detected. Thin contamination layers in the nm range may only be detected with difficulty.

Only comparatively thick layers in the μm range may also be analyzed in comparison to other technologies using x-ray fluorescence analysis (XFA). Nitrite layers may be detected especially well using the method. However, only smooth surfaces may be analyzed using this method. The method is especially suitable for examinations in the measurement laboratory, it is unsuitable for testing components on location in production.

Contaminations in the nm range may be assayed using electron spectroscopy. However, it requires a high apparatus outlay which is reflected in the costs for the method. In production, methods of this type may typically not be performed routinely because of the high outlay.

This is also true for electron microscopy and atomic force microscopy (electron force microscopy), using which contamination layers in the nanometer range are also detectable. Electron and atomic force microscopy also requires a high apparatus outlay, which is reflected in the cost for the method. In production, methods of this type may typically not be performed routinely because of the high outlay.

Hydrocarbon chains on the surface of components may be determined quantitatively using carbon determination through oxidation. The components to be assayed are heated to temperatures from 200° C. to 800° C. in a furnace. The temperature required is a function of the dirt composition. The hydrocarbon chains of organic contaminants are decomposed and desorbed, the carbon bonding in the furnace with the oxygen-containing transport gas to form a $CO/CO_2$ mixture. A conductivity measuring cell, in which the gas is admixed with sodium hydroxide (NaOH), is used for measuring the carbon content of the transport gas. It is possible to differentiate between different hydrocarbon chains by decomposition at different temperatures because of the differences in the carbon released.

SUMMARY OF THE INVENTION

The present invention is based on the object of allowing the testing of surfaces which are difficult to access, without the apparatus outlay growing.

This object is achieved according to the present invention by the cleaning method according to claim 1. Preferred embodiments of the present invention are the subject matter of the subclaims.

The present invention is based on the idea of detecting a contaminant rapidly and sensitively through visual comparison of a "dirt solution" and a reference solution. In particular a narrow area (solvent-water mixing zone) in a test tube is observed, in which the solution of dirt particles is especially noticeable.

The method according to the present invention for detecting residues on a surface of a component comprises the following steps: producing a base solution and a reference solution from water, producing a washing solution by adding fresh solvent to the base solution, filling the component to be tested with the washing solution, wetting the entire inner surface of the component with a washing solution, draining the washing solution out of the component, producing a test solution by adding the washing solution to the base solution, comparing the test solution to the reference solution and testing whether a turbidity occurs in the mixing zone between the washing solution and the base solution as evidence for lubricant on the surface of the component.

The method according to the present invention preferably has one or—if possible—multiple of the following features:

to produce the base solution and the reference solution, 9 ml water is placed in a test tube, the water being deionized or distilled;
to produce the washing solution, 1 ml fresh solvent is added using a Pasteur pipette to the base solution, so that a solvent-water mixing zone arises in the upper area of the test tube filling;
the component to be tested is filled approximately 5 to 10% of its empty volume with the washing solution, but with not more than 0.1 l of the washing solution;
the component is shaken and/or pivoted after passage of a predefined exposure time to improve the solution of the lubricant from the surface;
the exposure time is at least 10 minutes, and the shaking and pivoting is performed 10 to 15 times, the exposure time being doubled for complicated surfaces;
to produce the test solution, 1.0 ml of the used washing solution is decanted from above using a Pasteur pipette into a test tube which is filled with 9.0 ml water, the water being deionized or distilled and the test tube not being moved during decanting of the used washing solution;
2-propanol, denatured ethanol, or acetone is used to produce the washing solution.

An advantage of the present invention is that the present invention allows the testing of visually inaccessible surfaces. In the method according to the present invention, the complex (gas chromatography) assay of an extract or a residue of evaporation is dispensed with, the detection of the component purity is simplified, lubricants or lubricant components chemically dissolved in the solvent are also detected, the method according to the present invention may be used independently of the component size, it is independent of the ambient humidity, no measuring apparatus is necessary, it is independent of the chemical composition of the lubricant, no materials are used which result in deposits and/or corrosion nuclei in the hollow components and on other surfaces, the method according to the present invention may be applied to noble and base metals and to glass, ceramic, and many polymers, chemical reactions because of a testing method are avoided, no measuring apparatus are required, the method according to the present invention is independent of the layer thickness of the contamination, no analysis device is required, and the method is thus suitable for use on location.

BRIEF DESCRIPTION OF THE DRAWING

Further features and advantages of the present invention result from the following description of preferred exemplary embodiments, in which reference is made to the attached drawing.

DETAILED DESCRIPTION OF EMBODIMENTS

Figure 1:
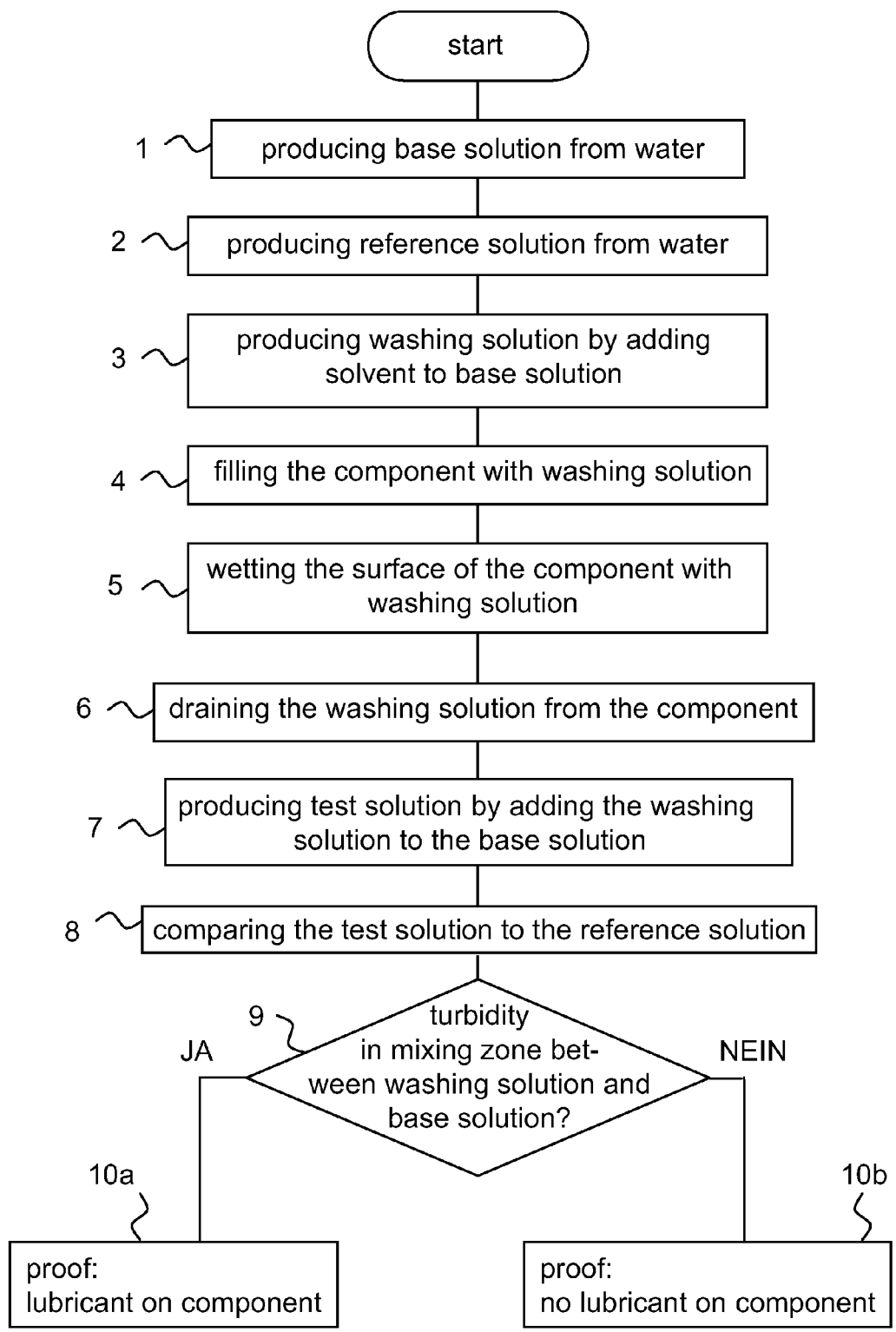

FIG. 1 shows the sequence of a preferred embodiment of the method according to the present invention.

In the method according to the present invention, whose sequence is shown in FIG. 1, 9 ml deionized or distilled water is placed as a base solution in a test tube, step 1. Parallel thereto, in step 2, a reference sample (also referred to as a blind value or null sample) of the same composition is produced, i.e., as 9 ml deionized or distilled water in a test tube.

To produce the actual washing solution, fresh solvent is added thereto using a clean Pasteur pipette in step 3 in such a way that a solvent-water mixing zone arises in the upper area of the test tube filling. The quantity of the solvent is preferably 1 ml. During the mixing, as a result of the change of the index of refraction of the mixture, a change of the transparency may occur, which does not represent turbidity, however, and disappears within a minute. If a permanent turbidity forms, the solvent and/or the water is contaminated and may not be used for performing the test. Water and solvent are then to be replaced by fresh substances.

The component to be tested is filled with the washing solution, step 4, an appropriate quantity of the washing solution being used. This washing solution quantity is a function of the volume of the component. Preferably, approximately 5 to 10% of the empty volume of the component is filled with solvent, the quantity is not to exceed 0.1 l for reasons of environmental protection, however. The component is closed by a fitted stopper and rotated and turned in such a way that the entire inner surface is wetted with the washing solution, step 5. In order to unfold its desired effect, the washing solution must act for at least 10 minutes. For complicated inner surfaces, the exposure time is doubled, so that all surfaces are wetted by the washing solution. In order to ensure the wetting of the entire surface, the component is preferably shaken or pivoted 10 to 15 times. The lubricant solution is thus improved by the flow of the washing solution along the surfaces of the component.

In step 6, the washing solution is drained out of the component. A test solution is produced using the used washing solution and the remaining clean base solution, step 7. For this purpose, 1.0 ml of the used washing solution is removed using a Pasteur pipette and added from above into a test tube, which is filled with 9.0 ml of the base solution, i.e., deionized or distilled water. The test tube is preferably fixed, so that it does not move and the washing solution and the base solution may be situated one over another in layers in the test tube.

If lubricant present on the component is dissolved by the solvent, turbidity which is more or less definite occurs in the test solution, which may be observed well in the mixing zone between the washing solution and the base solution. It may take up to 5 minutes until the turbidity occurs and/or is well recognizable in the test solution. How rapidly the turbidity occurs is a function of the type and the concentration of the lubricant. With some silicone lubricants and with lubricants based on polyfluorinated alkanes or perfluorinated polyethers, the method must be applied multiple times in some circumstances.

To recognize a turbidity in the test solution, in step 8, the test solution is preferably compared to the (clear) reference solution, in particular in the event of weak turbidities. After it has been established in step 9 whether a turbidity exists or not, the proof is furnished, either the lubricant is present on the component, step 10*a*, since in comparison to the reference a turbidity is recognizable, or no lubricant is present on the component, step 10*b*, since no turbidity is recognizable in comparison to the reference.

Only 2 test tubes, 2 Pasteur pipettes having a volume of 1.0 ml, a measuring cylinder having a volume of 10.0 ml, and a beaker, as well as diverse stoppers for the component to be assayed, are required for performing the method according to the present invention.

It is essential in the method according to the present invention that all devices used are clean and free of lubricant. Contaminated devices result in false results and therefore may not be used. In addition, only water-soluble liquids come into consideration as the solvent. If the solvent used is poorly soluble or insoluble in water, no mixing zone or only a very limited mixing zone arises. A turbidity may not occur even though lubricant is dissolved, and incorrectly result in the statement "component clean". Solvents with poor or limited water solubility may cause a turbidity with the water in the mixing zone and simulate a lubricant content. The solvent used must have the degree of purity p.a. (pro analysi). The degree of purity is specified on the chemical bottle by the producer. The use of solvent of lower quality may result in false test results and is not permissible. Distilled or deionized water is to be used for the reference test and for the assay of the solvent applied to the component. If other water qualities are used, interference in the recognition of the turbidity in the samples and/or in the reference may occur. Sample and reference may then no longer be compared to one another.

The present invention is suitable for small components which may be lifted and turned easily by one person alone.

For reasons of work and environmental protection, the quantity of the solvent used is preferably limited to at most 0.1 l.

The temperature of the component surface to be cleaned may not exceed the boiling point of the solvent used, since it then vaporizes immediately. Temperatures of over 25° are preferably avoided, since many solvents vaporize noticeably then and the lubricant solution becomes worse. Temperatures below +0.1° C. are preferably also avoided, since aqueous lubricant systems may then be partially or entirely frozen and may withdraw entirely or partially from being dissolved by the solvent.

In an experimental series, it was observed that lubricant only partially dissolves in the solvent. The solution of the lubricant is thus not complete and does not replace component cleaning. Acetone has been shown to be the most suitable solvent in the experiment in comparison to 2-propanol and denatured ethanol. Through IR spectral recordings of the lubricants used in the acetone extracts in the laboratory, it was able to be verified that lubricants were at least partially dissolved by acetone and the turbidities observed upon dilution of the acetone extracts with water were to be attributed to the lubricant or lubricant components dissolved in the acetone.

The advantages of the present invention are, inter alia, that the present invention provides the result of the assay of the degree of contamination within a few minutes. Furthermore, the present invention may be applied to all solvent-resistant surfaces, such as glass, steels, ceramic, and many polymer materials. In addition, the present invention may be applied without the presence of a water or power connection, i.e., "in the field" or in running production. No specially trained personnel are required for performing the lubricant detection method described in the scope of the present invention. Laboratory instruments or testing devices are also not required. Some consumable materials such as solvent, deionized or distilled water, and Pasteur pipettes are necessary. No costs are thus caused by the application of the present invention. In addition, the method according to the present invention displays high efficiency, in particular if the lubricant entirely or partially dissolves in the washing solution. The method according to the present invention is thus equal to other detection methods which are based on dissolving, and it manages without further laboratory analysis. The method according to the present invention is also independent of the thickness of the lubricant layer.

REFERENCE SIGNS

1 production of base solution from water
2 production of reference solution from water
3 production of washing solution by adding solvent to base solution
4 filling the component with washing solution
5 wetting the surface of the component with washing solution
6 draining the washing solution from the component
7 producing test solution by adding the washing solution to the base solution
8 comparing the test solution to the reference solution
9 query: turbidity in mixing zone between washing solution and base solution?
10 proof: 10*a* lubricant on component, 10*b* no lubricant on component

The invention claimed is:

1. A method for detecting lubricant residues on an inner surface of a component, which comprises the following steps:
producing a base solution and a reference solution from water,
producing a washing solution by adding fresh water soluble solvent to the base solution,
filling the component to be tested with the washing solution,
wetting the inner surface of the component with the washing solution,
draining the washing solution from the component,
producing a test solution by adding the washing solution to the base solution,
comparing the test solution to the reference solution; and
testing whether a turbidity occurs in the mixing zone between the washing solution and the base solution, as proof of lubricant residues on the inner surface of the component.

2. The method according to claim 1, wherein to produce the base solution and the reference solution, 9 ml water is placed in a test tube, the water being deionized or distilled.

3. The method according to claim 2, wherein to produce the washing solution, 1 ml fresh solvent is added using a Pasteur pipette to the base solution, so that a solvent-water mixing zone arises in the upper area of the test tube filling.

4. The method according to claim 1, wherein the component to be tested is filled to approximately 5 to 10% of the empty volume with the washing solution, but with less than 0.1 l of the washing solution.

5. The method according to claim 1, wherein the component is actuated by at least one of a shaking and pivoting movement after passage of a predefined exposure time to improve the solution of the lubricant from the surface.

6. The method according to claim 5, wherein the exposure time is at least 10 minutes and the shaking and pivoting is performed 10 to 15 times, the exposure time being doubled for complicated surfaces.

7. The method according to claim 1, wherein to produce the test solution, 1.0 ml of the used washing solution is decanted from above into a test tube using a Pasteur pipette, which is filled with 9.0 ml water, the water being deionized or distilled and the test tube not being moved during the decanting of the used washing solution.

8. The method according to claim 1, wherein 2-propanol, denatured ethanol, or acetone is used as the solvent for producing the washing solution.

* * * * *